United States Patent [19]

Sprecker

[11] 4,357,319
[45] Nov. 2, 1982

[54] ALKENYL PHENETHYLETHERS AND USES THEREOF IN COMBATTING TOBACCO BEETLES

[75] Inventor: Mark A. Sprecker, Sea Bright, N.J.

[73] Assignee: International Flavors & Fragrances Inc., New York, N.Y.

[21] Appl. No.: 337,738

[22] Filed: Jan. 7, 1982

Related U.S. Application Data

[62] Division of Ser. No. 238,750, Feb. 27, 1981, Pat. No. 4,328,206.

[51] Int. Cl.³ .............................................. A01N 17/14
[52] U.S. Cl. ...................................................... 424/84
[58] Field of Search ............................................ 424/84

[56] References Cited

U.S. PATENT DOCUMENTS 2,469,228  5/1949  Gertler ................................. 424/339
4,306,096  12/1981  Kiwala et al. ......................... 424/84
4,324,923  4/1982  Kiwala et al. ......................... 424/84

Primary Examiner—Donald B. Moyer
Attorney, Agent, or Firm—Arthur L. Liberman

[57] ABSTRACT

Described are the compounds, alkyl and alkenyl phenethylether derivatives, defined according to the structure:

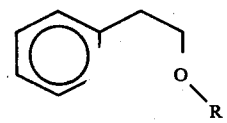

wherein R represents $C_3$ or $C_6$ secondary alkyl (2°-alkyl) or $C_4$ alkenyl which have, individually or in combination, been found to be useful in augmenting or enhancing the aroma of perfumes and perfumed articles as well as colognes and, in addition, in combatting tobacco beetles of the species *Lasioderma serricorne* (F.).

3 Claims, 13 Drawing Figures

GLC PROFILE FOR EXAMPLE I(A).

NMR SPECTRUM FOR EXAMPLE I(A).

IR SPECTRUM FOR EXAMPLE I(A).

GLC PROFILE FOR EXAMPLE I(B).

GLC PROFILE FOR EXAMPLE II OF FRACTION 4.

GLC PROFILE FOR EXAMPLE II, PRIOR TO PROPIONIC ANHYDRIDE REACTION.

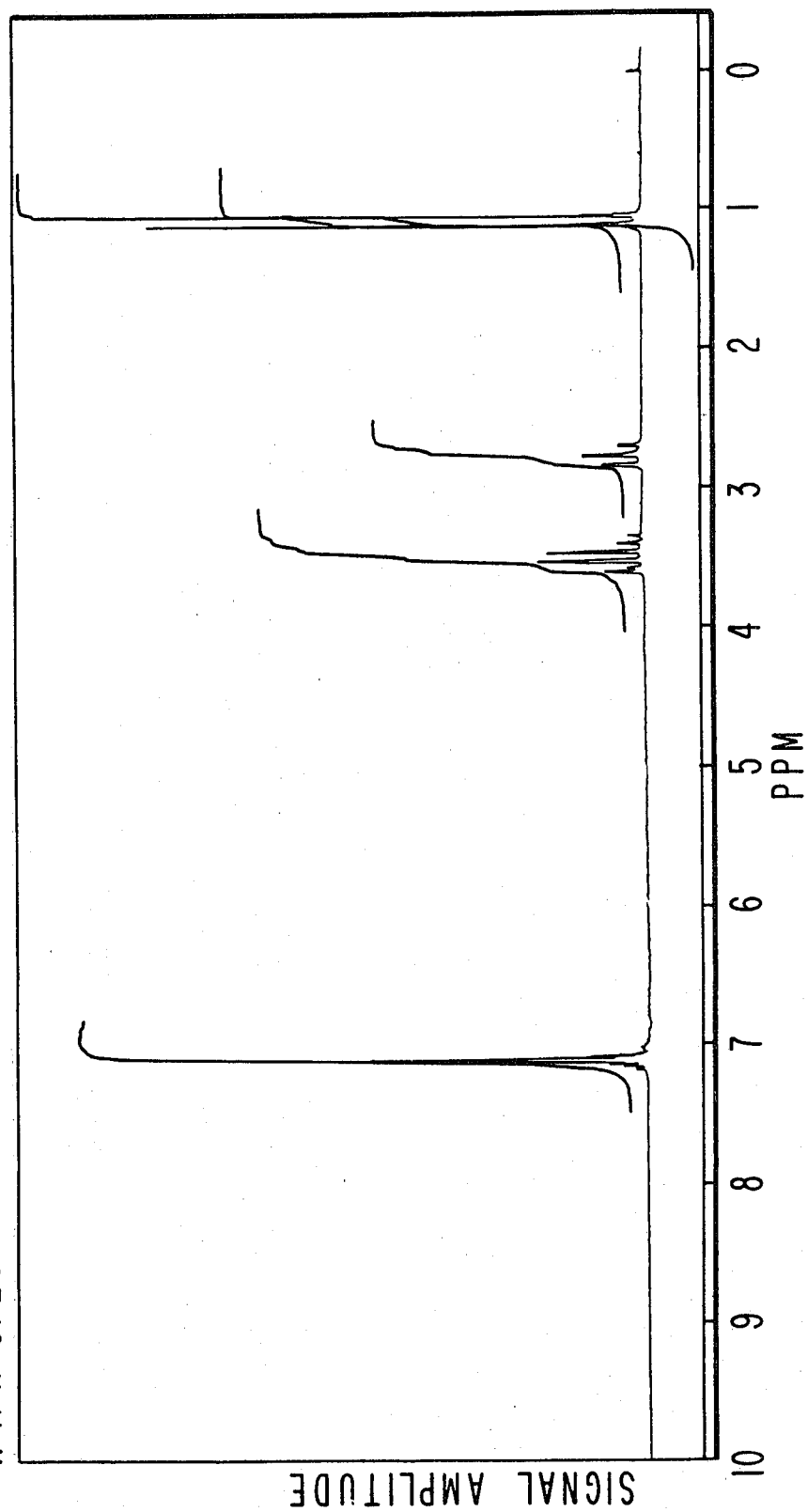

IR SPECTRUM FOR EXAMPLE II.

GLC PROFILE FOR EXAMPLE III. (CRUDE)

NMR SPECTRUM FOR PEAK 4 OF FIG. 9 OF EXAMPLE III.

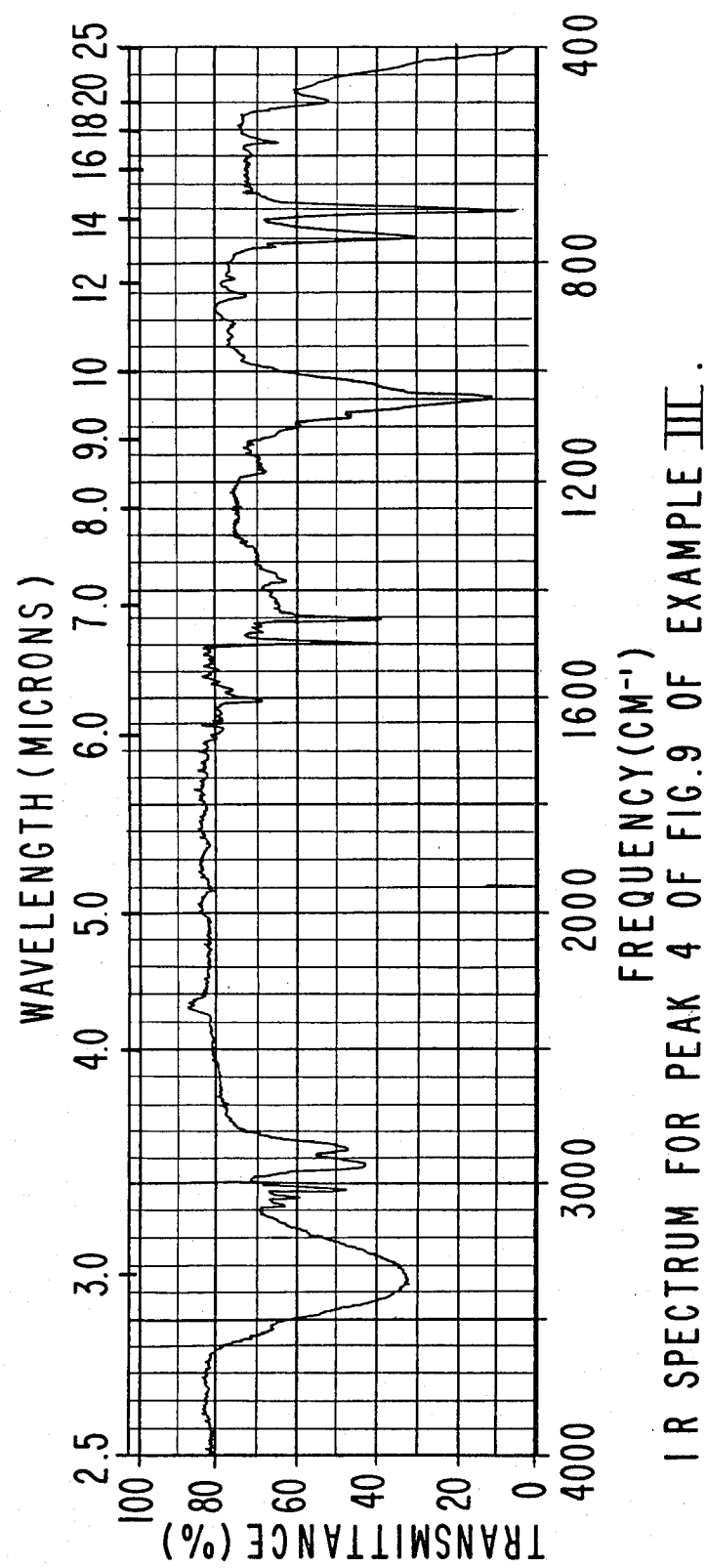

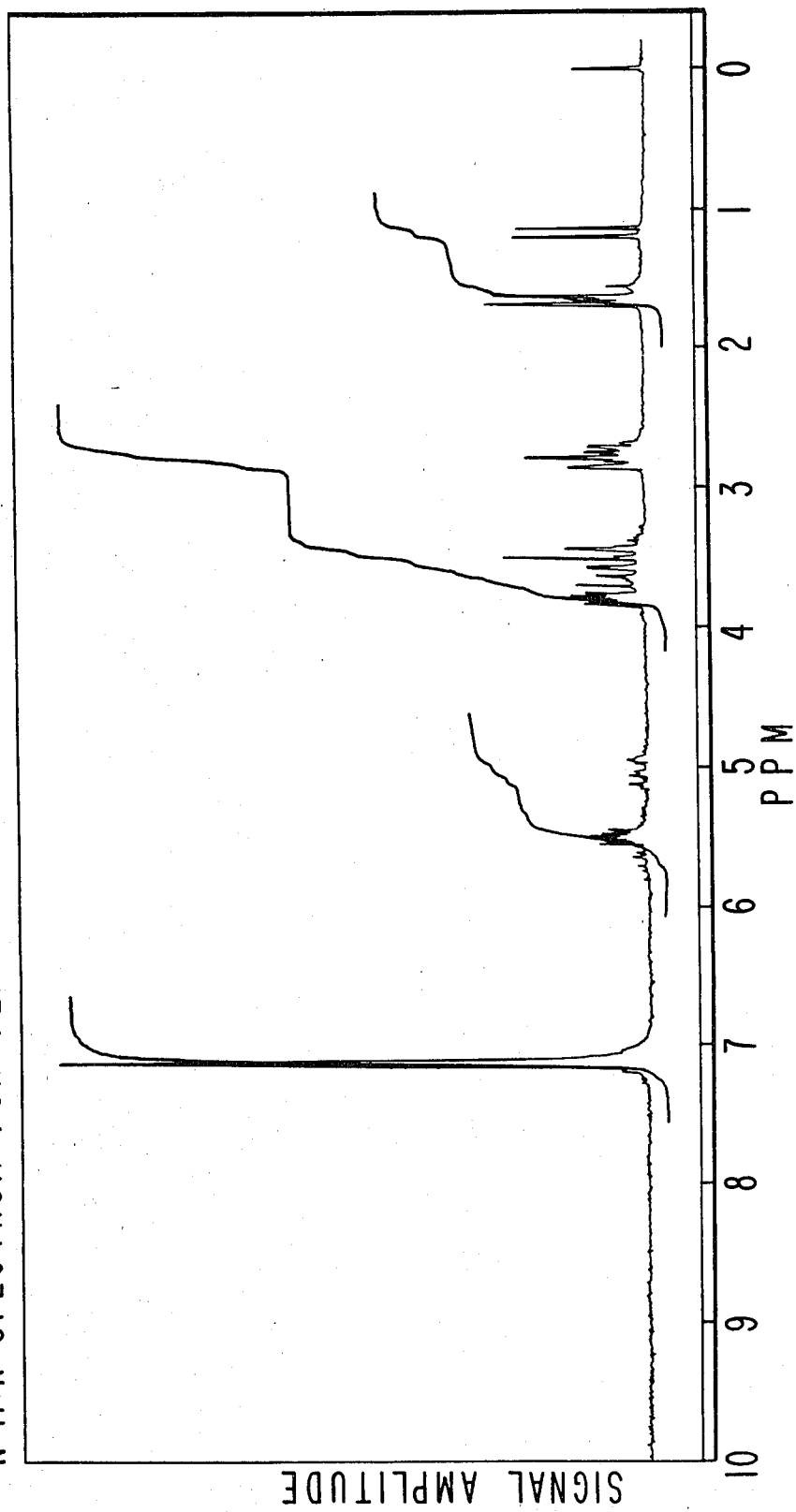
FIG. II A
NMR SPECTRUM FOR PEAK 5 OF FIG. 9 OF EXAMPLE III.

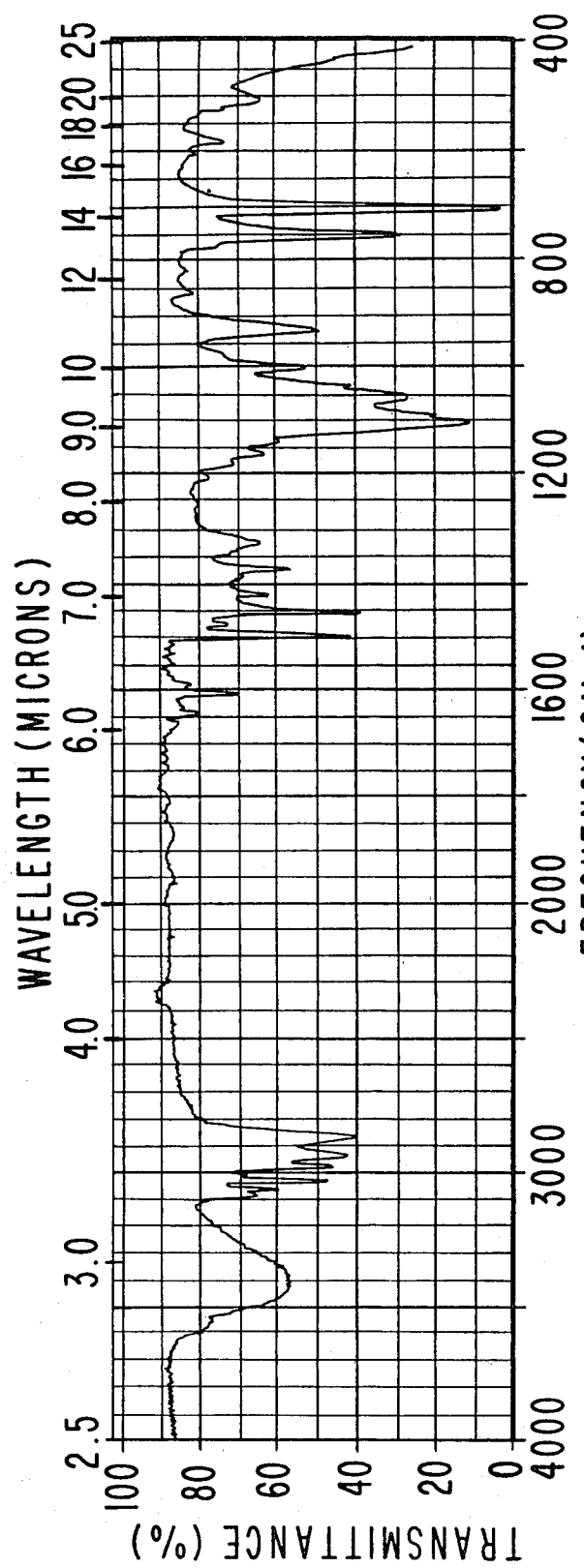
FIG.IIB
IR SPECTRUM FOR PEAK 5 OF FIG.9 OF EXAMPLE III

ALKENYL PHENETHYLETHERS AND USES THEREOF IN COMBATTING TOBACCO BEETLES

This is a divisional of application Ser. No. 238,750, filed Feb. 27, 1981, now U.S. Pat. No. 4,328,206.

BACKGROUND OF THE INVENTION

This invention relates to phenethyl alkyl and alkenyl ethers and to the uses thereof in combatting insects as a result of the discovery that the alkyl and alkenyl phenylethers are tobacco beetle pheromones or ectohormones; and in addition to the uses of phenethyl alkyl or alkenyl ethers in augmenting or enhancing the aromas of perfumes, colognes and perfumed articles (e.g., solid or liquid anionic, cationic, nonionic and zwitterionic detergents, fabric softeners, fabric softener articles, hair conditioners, odorants and deodorants). Obviously then, the invention also relates to one or more pleasant smelling pheromones or ectohormones useful for combatting insects yet, at the same time, not repulsive to the individual or group of individuals applying the pheromone or ectohormone to the area where the insects are to be combatted.

Pheromones or ectohormones are secreted by insects as so called socially active ingredients, e.g., as sexual attractants or aggregation substances. The use of these pheromones or ectohormones is known to attract insects into certain small sections of a contaminated area, to concentrate them in this are and then to destroy the insects in any known way, e.g., mechanically, chemically or with insecticides. This method leads to a very economical and concentrated use of the actual insecticides, especially of insecticides which are ecologically dangerous, whereby the spraying of large parts of the contaminated area in an expensive way, e.g., by spraying insecticides with an aeroplane, is avoided.

No pheromones have been discovered up to the present time for use with *Lasioderma serricorne* (F.) with the exception of cyclohexyl phenethylethers as described in co-pending application for U.S. patent, Ser. No. 192,238 now U.S. Pat. No. 4,306,096. Thus, the pheromones known up to the present time with the exception of the cyclohexyl phenethylethers of application for U.S. patent, Ser. No. 192,238 belong to a large variety of chemical substances and are, as a rule, effective only with respect to certain insects such as, for example, for use in combatting insects of the order coleoptera and the finally scolytidae and platypodidae which beetles cause substantial damage to forests and to the wood of trees generally as taught in U.S. Pat. No. 3,927,207 issued on Dec. 16, 1975.

Another problem as yet unsolved by the prior art with the exception of the use of cyclohexyl phenethylethers as described in application for U.S. patent, Ser. No. 192,238 concerns the utilization, either in conjuction with or as pheromones or ectohormones for insect attractants, of fragrance imparting, augmenting or enhancing agents. Such fragrance imparting, augmenting or enhancing agents must be either identical to or, at the very least, compatible with the pheromones or ectohormones. Previously such pheromones or ectohormones having their own aroma profiles have been found to have an aroma profile which either was esthetically displeasing or, at the very best, incapable of covering or deodorizing the chemical-like sharp, abrasive aroma of the insecticides used against the insects; that is, prior to the finding of the cyclohexyl phenethylethers of application for U.S. patent, Ser. No. 192,238, filed on Sept. 30, 1980.

An optimal solution to the foregoing problems would be to create, in one chemical, a pheromone or ectohormone; an insecticide; and an aroma augmenting or enhancing substance which is compatible with said pheromone or ectohormone and with said insecticide.

Notwithstanding the aforementioned pheromone or ectohormone properties and notwithstanding the aforementioned insecticide properties, chemical compounds which can provide green, fruity, floral, hyacinth-like, rosy, rose-hyacinth-like, galbanum-like, cassis-like and narcissus-like aromas with hyacinth/honey aroma on dry-out and with peppery and mushroom undertones which are both rich and full-bodied as well as long-lasting are desirable in the art of perfumery. Many of the natural materials which provide such fragrances and contribute such desired nuances to perfumery compositions are high in cost, unattainable at times, vary in quality from one batch to another and/or are generally subject to the usual variations of natural products.

There is, accordingly, a continuing effort to find synthetic materials which will replace, enhance or augment the fragrance notes provided by natural essential oils or compositions thereof. Unfortunately, many of these synthetic materials either have the desired nuances only to a relatively small degree or else contribute undesirable or unwanted odor to the compositions. The search for materials which can provide more refined, more natural-like, more long-lasting green, fruity, floral, hyacinth-like, rosy, rose-hyacinth-like, galbanum, cassis-like and narcissus-like aromas with hyacinth/honey aromas on dry-out and peppery and mushroom undertones has been difficult and relatively costly in the areas of both natural products and synthetic products.

Arctander in "Perfume and Flavor Chemicals (Aroma chemicals)", Volume II, 1969 describes phenylethyl alcohol as having a rose aroma.

The use in perfumery of alkyl ethers of phenylethyl alcohol is known. Thus, Chem. Abstracts, Volume 79, 1973, 18356m abstracts U.S. Pat. No. 3,734,970 which discloses the use of phenylethyl alcohol methylether having the structure:

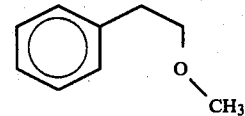

in perfumery. It is further indicated that this material is produced by reaction of phenylethyl alcohol with a mercury-aluminum couple to form triphenylethoxy aluminum and reacting the triphenylethoxy aluminum with dimethoxysulfoxide to form the phenylethyl alcohol methylether.

Chem. Abstracts, Volume 87, 1977, 87:135063q discloses the genus of compounds having the structure:

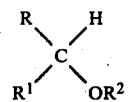

which abstracts Japanese Kokai No. 77-07,911 and uses of these compounds in perfumery wherein R represents alkyl, alkenyl, alkynyl, aryl, aralkyl and cycloalkyl and $R^1$ represents hydrogen or R and $R^2$ represents alkyl or phenylalkyl.

Chem. Abstracts 90:127414, Volume 90 (1979) abstracts French Demande No. 2,373,276 which discloses the use of the compound having the structure:

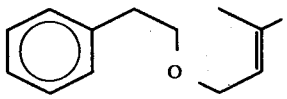

synthesized according to the reaction sequence:

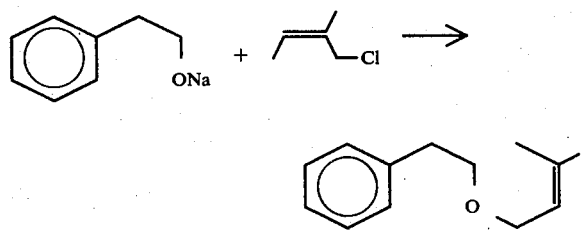

in perfumery particularly as a lilac perfumant.

Nothing in the prior art, however, discloses the specific compounds having the structures defined according to the genus:

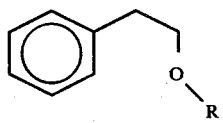

wherein R is $C_3$ or $C_6$ 2°-alkyl or $C_4$ alkenyl.

Phenylethyl alcohol isoamylether has been used for several years in the perfumery industry but has been found to have an undesirable "chocolate" nuance. Phenylethyl alcohol isoamylether has the structure:

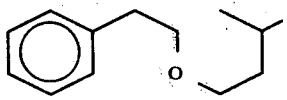

and is a "primary" alkyl ether rather than a "secondary" alkyl ether.

Isobutyl phenylacetate (otherwise known as "Anther") having the structure:

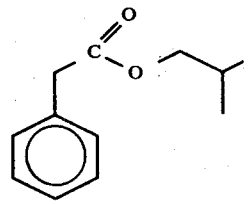

an ester, is described by Arctander "Perfume and Flavor Chemicals (Aroma Chemicals)" 1969 as being extensively useful in perfumery for fresh "petal" notes in rose, peony, narcisse, carnation, sweet pea, freesia and hyacinth. Arctander also indicates that this material is on a "GRAS" list as having number 2210.

Arctander also indicates at monograph number 514 that isobutyl phenylether having the structure:

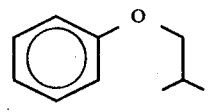

has a harsh chemical odor, sweet but with a metallic chemical background and being remotely reminiscent of anise.

Phenethyl propionate has been disclosed in the Journal of Economic Entomology, 66, (5), 1973, and has been indicated by McGovern et al to be an attractant for *Popillia japonica* Newman (Japanese beetles) particularly in combination with eugenol. Indeed, in that same paper by McGovern et al., it is indicated that trans-2-hexanal, a well-known perfume ingredient, is also a Japanese beetle attractant. The phenethyl propionate has the structure:

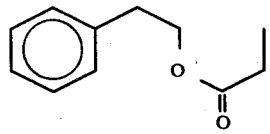

In another paper by McGovern et al., Journal of Economic Entomology, Volume 63, Number 1, page 276, it is indicated that methyl cyclohexanepropionate and certain related chemicals are also attractants for *Popillia japonica* Newman.

Research concerning *Lasioderma serricorne* (F.) and attractants therefor are limited to the use of extracts of natural food odors. Thus, the paper by Fletcher and Garrett entitled "Ovipositional Response of Three Strains of the Cigarette Beetle to Extracts of Food Odors" in Tobacco International, 182 (5), pages 166–169, Mar. 7, 1980. Fletcher and Garrett disclose that the ovipositional response of three strains of the cigarette beetle is a function of different food odor attractants.

Nothing in the prior art, however, discloses the unexpected, unobvious and advantageous properties of the phenethylether derivatives having the generic structure:

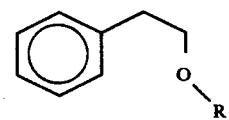

wherein R represents $C_3$ or $C_6$ 2°-alkyl or $C_4$ alkenyl which are not only useful per se for augmenting or enhancing the aroma of perfume compositions, colognes and perfumed articles, but are also useful individually or taken in combination as *Lasioderma serricorne* (F.) pheromones and, in addition, as *Lasioderma serricorne (F.) insecticides*.

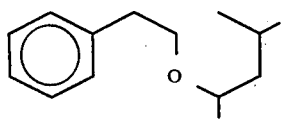

Figure 2:
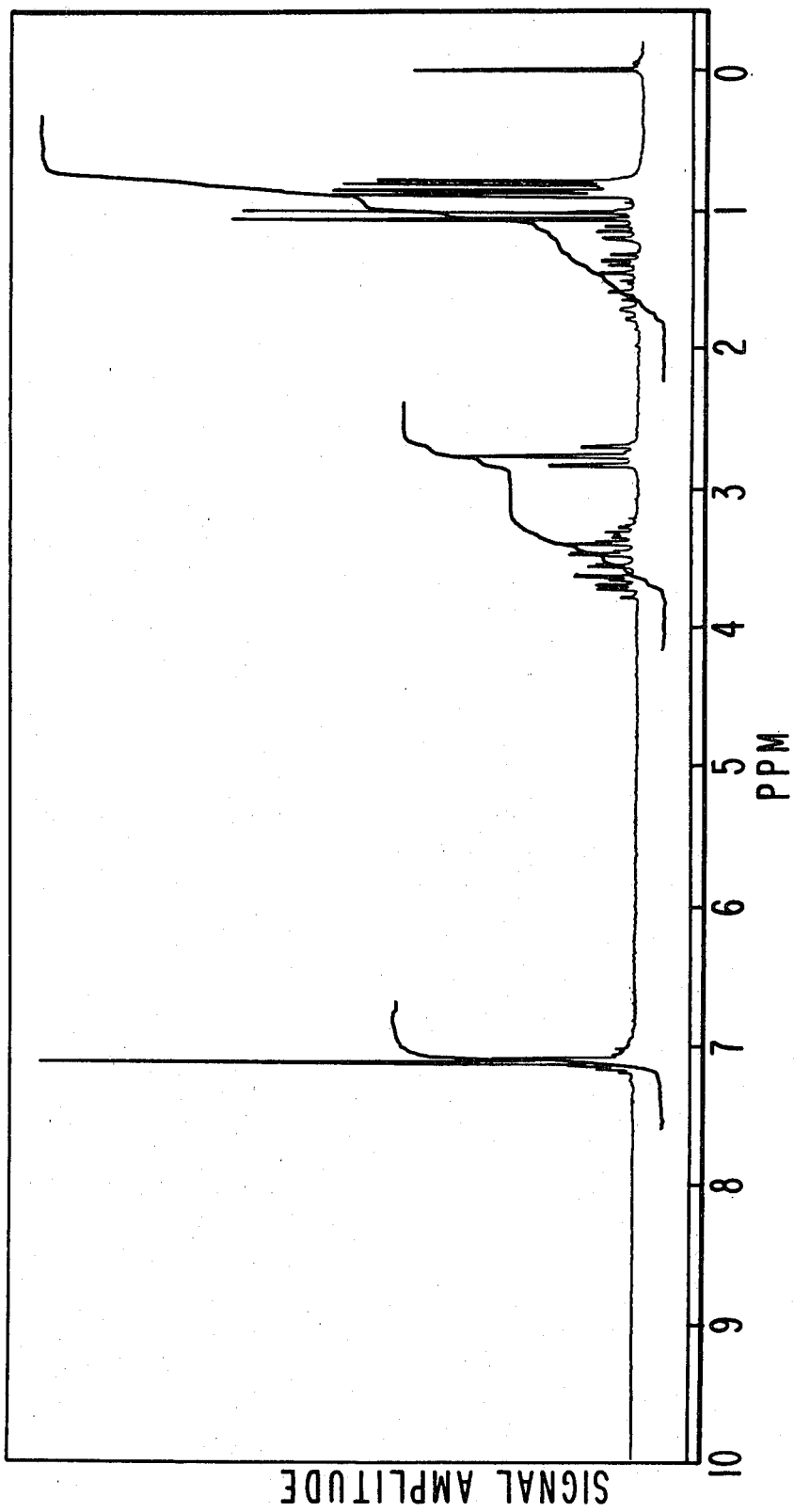

FIG. 2 is the NMR spectrum for the reaction product of Example IA containing the compound having the structure:

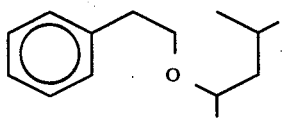

Figure 3:
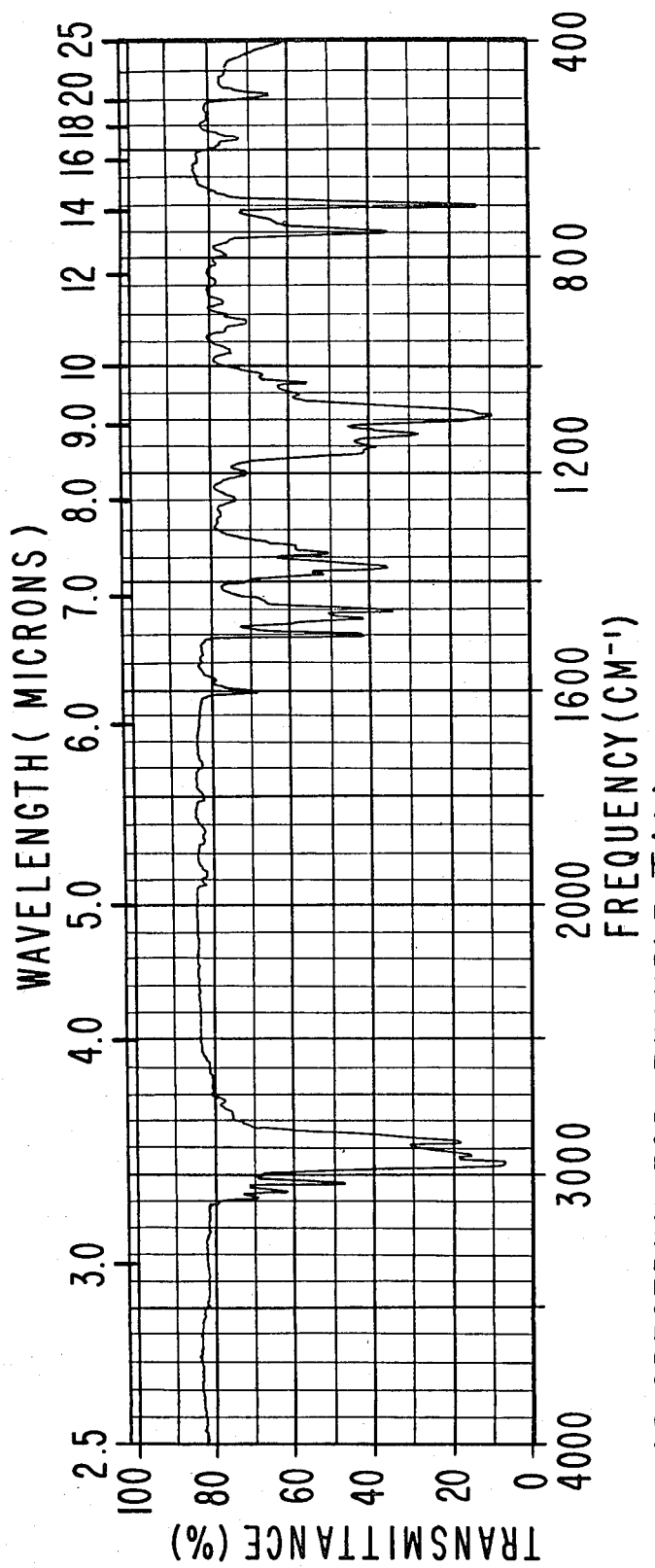

FIG. 3 is the infra-red spectrum for the reaction product of Example IA containing the compound having the structure:

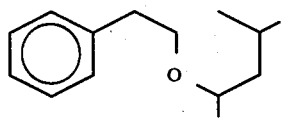

Figure 4:
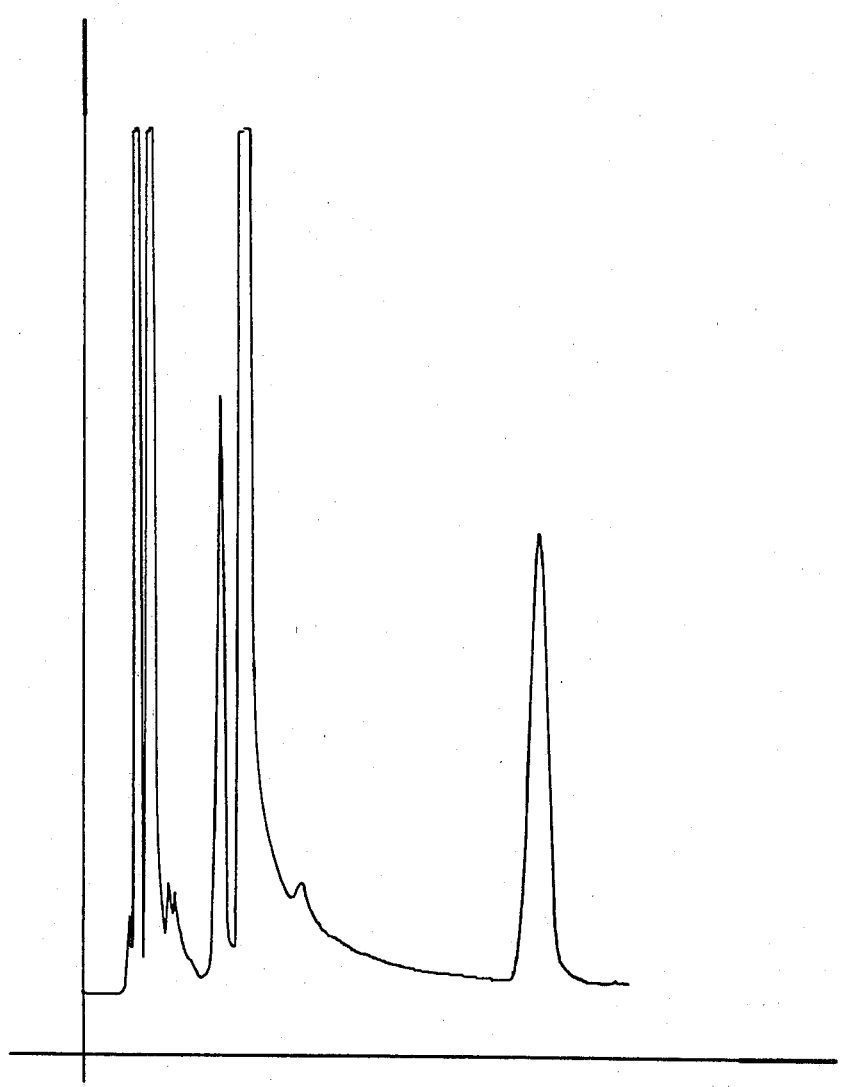

FIG. 4 is the GLC profile for the crude reaction product of Example IB containing the compound having the structure:

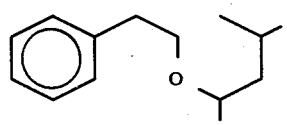

Figure 5:
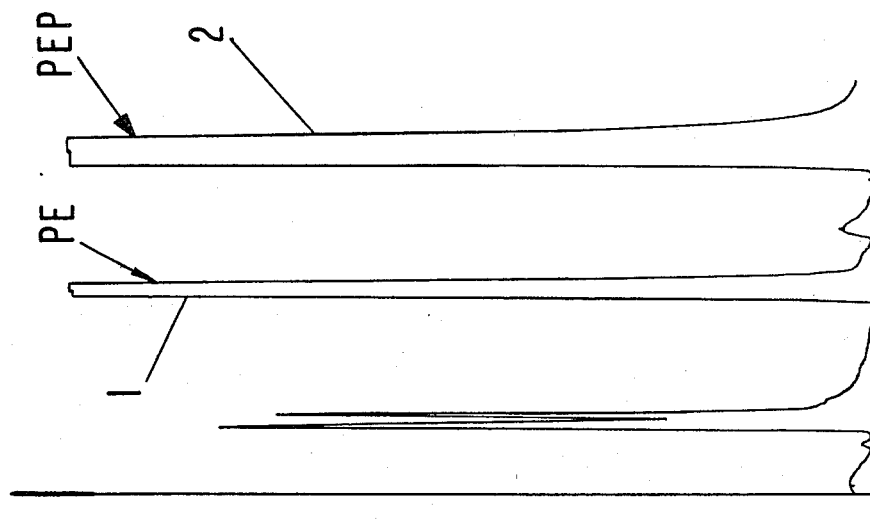

FIG. 5 is the GLC profile for the crude reaction product of Example II prior to propionic anhydride reaction containing the compounds having the structures:

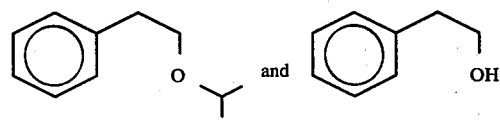

Figure 6:
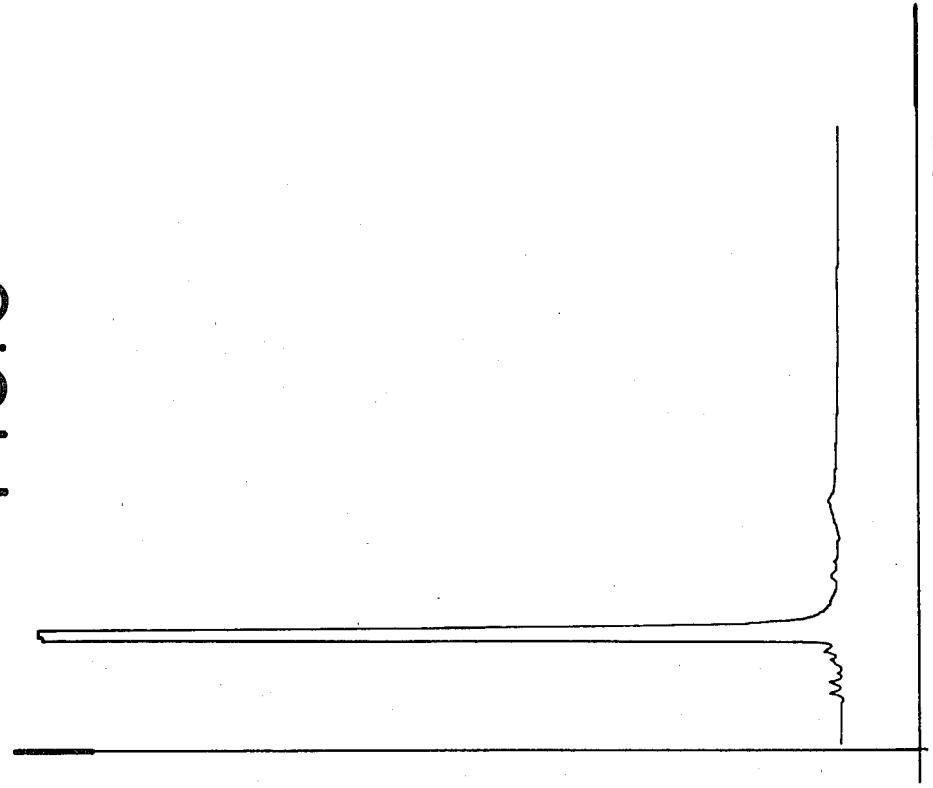

FIG. 6 is the GLC profile for fraction 4 of the distillation product of the reaction product of Example II after reaction with propionic anhydride, containing the compound having the structure:

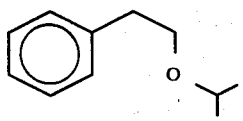

Figure 8:
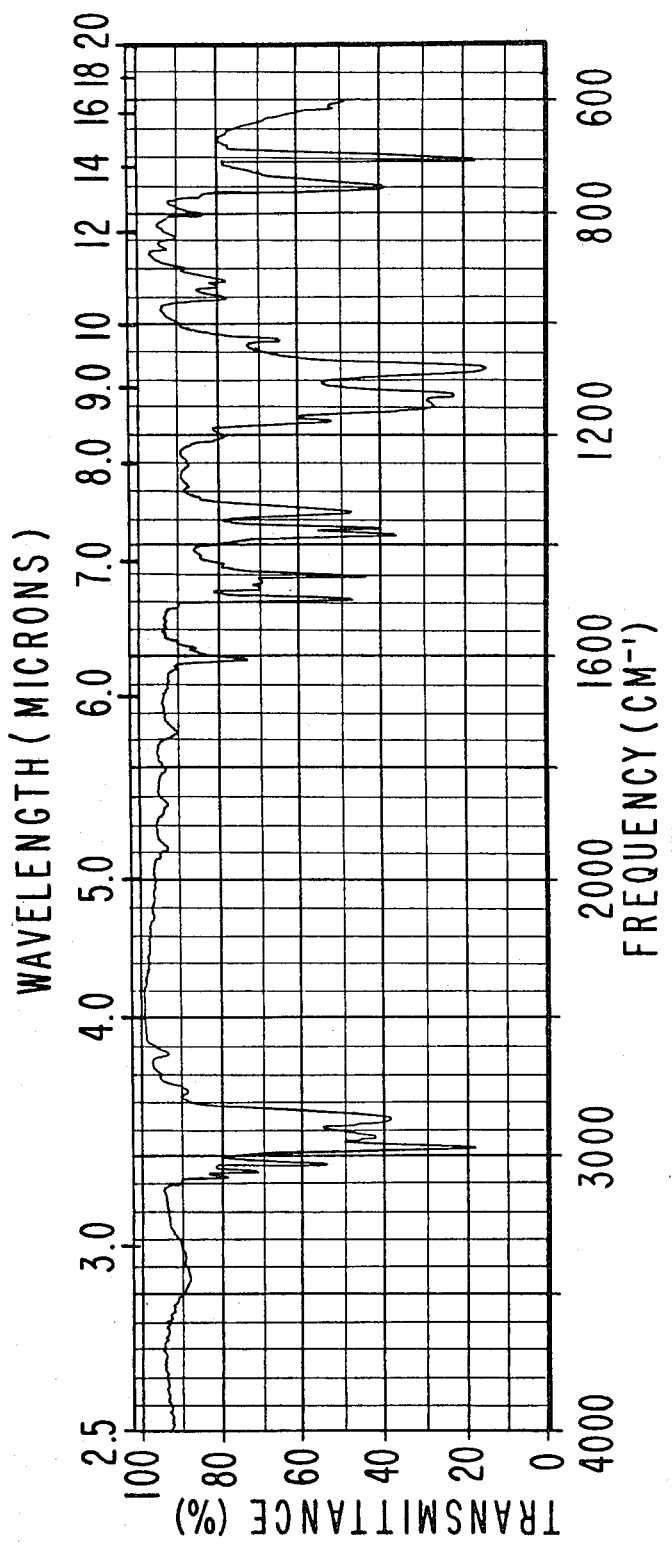

FIG. 7 is the NMR spectrum for the reaction product of Example II after distillation containing the compound having the structure:

FIG. 8 is the infra-red spectrum for the reaction product of Example II after distillation after reaction with propionic anhydride containing the compound having the structure:

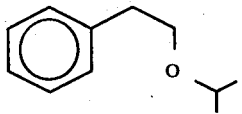

Figure 9:
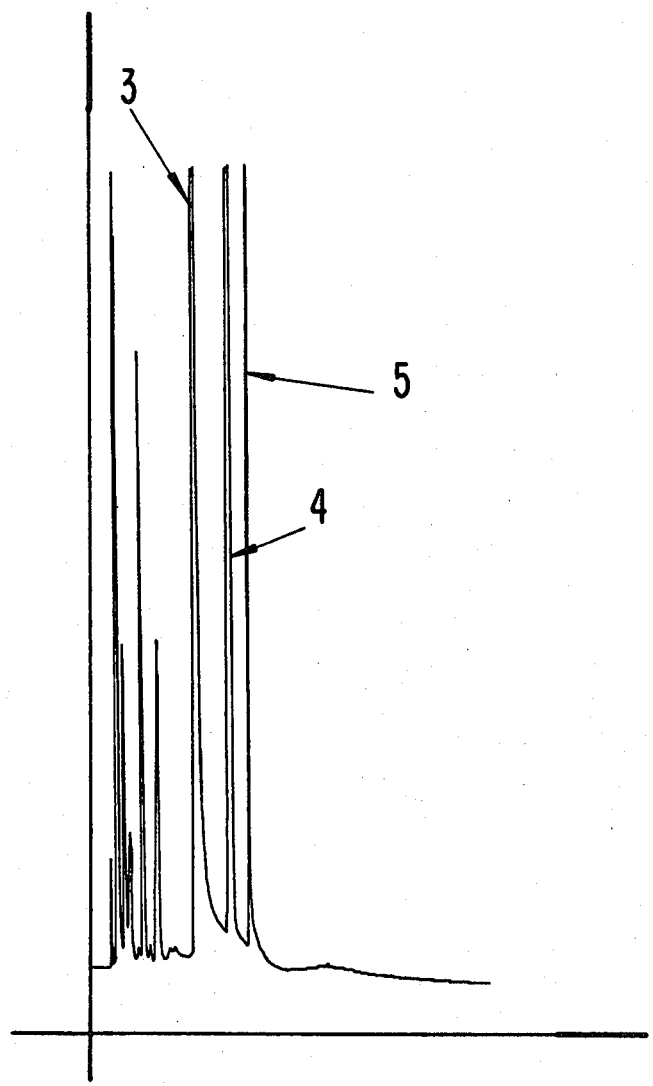

FIG. 9 is the GLC profile of the reaction product of Example III containing the compounds having the structures:

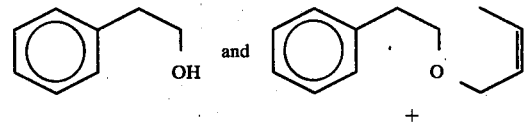

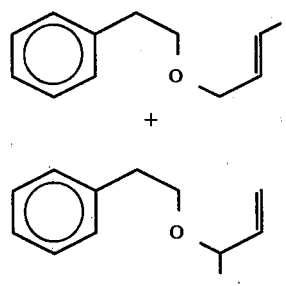

Figure 10A:
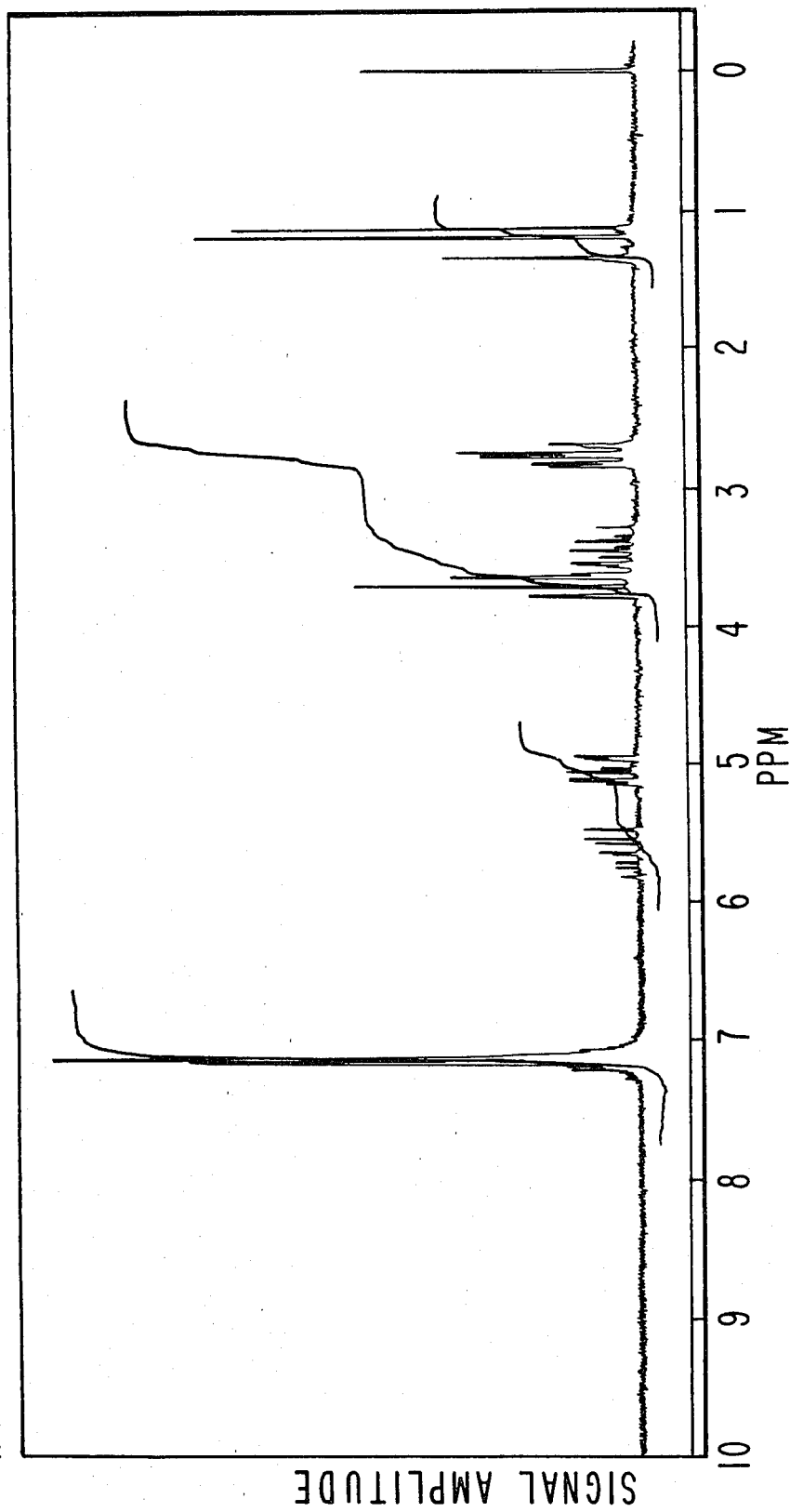

FIG. 10A represents the NMR spectrum for peak 4 of the GLC profile of FIG. 9 containing the compound having the structure:

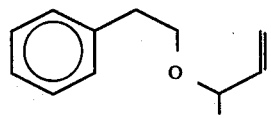

FIG. 10B is the infra-red spectrum for peak 4 of FIG. 9 which is the GLC profile for the reaction product of Example III, containing the compound having the structure:

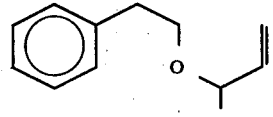

FIG. 11A is the NMR spectrum for peak 5 of FIG. 9 which is the GLC profile for the reaction product of Example III, containing the compounds having the structures:

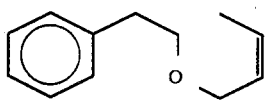

+

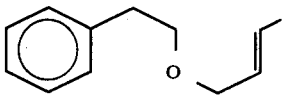

FIG. 11B is the infra-red spectrum for peak 5 of FIG. 9 which is the GLC profile of Example III, containing the compounds having the structures:

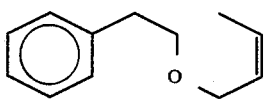

+

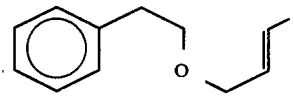

DETAILED DESCRIPTION OF THE DRAWINGS, FIGS. 5 and 9

FIG. 5 is the GLC profile for the crude reaction product of isopropanol and phenylethyl alcohol having the structure:

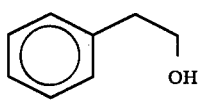

which contains the compounds phenylethyl alcohol isopropyl ether having the structure:

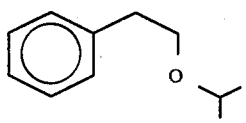

and phenylethyl alcohol having the structure:

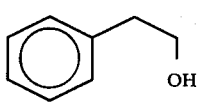

The peak indicated by the reference numeral "1" represents phenylethyl alcohol having the structure:

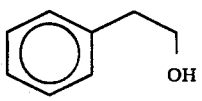

The peak indicated by the reference numeral "2" represents the phenylethyl alcohol isopropyl ether having the structure:

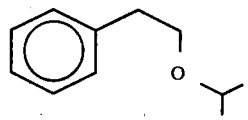

These two compounds are virtually impossible to separate by distillation and require reaction with propionic anhydride followed by separation of the resultant phenylethyl alcohol isopropyl ether and phenylethyl alcohol propionate having the structure:

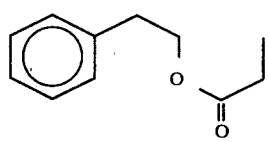

FIG. 9 is the GLC profile for the reaction product of Example III. The reaction product of Example III contains four compounds:

phenylethyl alcohol having the structure:

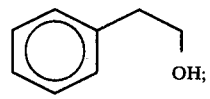

2-butenol phenylethylether, cis-isomer and trans-isomer having the structures:

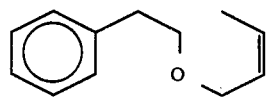

+

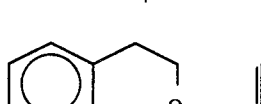

and phenylethyl methallylether having the structure:

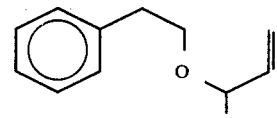

The peak on the GLC profile indicated by the reference numeral "3" is the peak for phenylethyl alcohol having the structure:

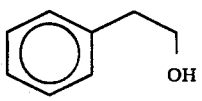

The peak on the GLC profile of FIG. 9 indicated by the reference numeral "4" is the peak for the phenylethylether of methallyl alcohol having the structure:

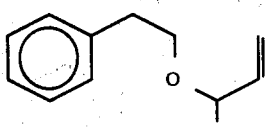

The peak on FIG. 9, the GLC profile, indicated by the reference numeral "5" is the peak for the phenylethylether of 2-butenol, both the "cis" and "trans" isomers having the structures:

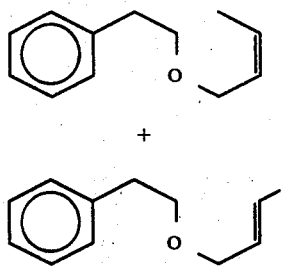

THE INVENTION

The present invention proposes the use of certain phenethylethers which are alkyl phenethylethers or alkenyl phenethylethers defined according to the generic structure:

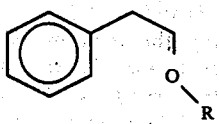

wherein R represents $C_3$ or $C_6$ 2°-alkyl or $C_4$ alkenyl for combatting beetles of the order *Lasioderma serricorne* (F.) in such a manner that one or a combination of the alkyl or alkenyl phenethylethers not only acts as a pheromone or ectohormone but also acts as an aroma augmenting or enhancing agent and, in addition, acts as an insecticide. Notwithstanding the pheromone and insecticide properties of the alkyl and alkenyl phenethylethers, the instant invention also provides alkyl and alkenyl ethers as fragrances capable of augmenting or enhancing the fragrances of perfume compositions, colognes and perfumed articles (e.g., solid or liquid anionic, cationic, nonionic or zwitterionic detergents, fabric softeners, dryer-added fabric softener articles, hair conditioners, deodorants and cosmetic powders).

The alkyl and alkenyl phenethylethers of our invention are capable of augmenting or enhancing the green, fruity, floral, hyacinth-like, rosy, rose-hyacinth-like, galbanum-like, cassis-like and narcissus-like aromas of perfumes, perfumed articles and colognes of our invention. Of course, as part of the perfumed articles of our invention is the "perfumed insecticide-pheromone" compositions of our invention.

The destruction of the *Lasioderma serricorne* (F.) insects can be achieved by distributing one or a combination of the alkyl and/or alkenyl phenethylethers (which act as pheromonal attractants) in the contaminated area at separate individual places, namely, by means of catch trees. These are impregnated with the attractants which may, if desired, act as an insecticide too; or the alkyl and/or alkenyl phenethylethers may be augmented by additional insecticides whereupon the catch trees are sprayed with another insecticide either before or after the insects have gathered at the catch tree (whatever insects are still alive after contact with the alkyl and/or alkenyl phenethylethers). Instead of using the alkyl and/or alkenyl phenethylethers alone or taken together with another insecticide, one may also use a chemical sterilizing compound. Further, the catch tree may be treated with other chemicals or can be burned. Another possible method for destroying insects with the alkyl and/or alkenyl phenethylethers according to our invention makes use of the disturbance or perturbance theory. Instead of physically destroying the insects with either high concentrations of the alkyl and/or alkenyl phenethylethers or by using the alkyl and/or alkenyl phenethylethers followed by an additional insecticide, it is also possible to combine the alkyl and/or alkenyl phenethylethers physically with another stronger insecticide before using. Thus, it is possible now to spray a combination of alkyl and/or alkenyl phenethylethers which have pleasant aromas in combination with insecticides whose original aroma(s) is covered using the alkyl and/or alkenyl phenethylethers in certain centrally located areas or in the form of rows in the contaminated area. Furthermore, the alkyl and/or alkenyl phenethylethers can be mixed with the usual solid or liquid carriers or with biocides such as stronger insecticides, pesticides or herbicides. The mixture may contain surface active agents to obtain a better distribution or adherence to the plants.

The alkyl and/or alkenyl phenethylethers of our invention may be prepared by reacting β-phenylethyl alcohol with an appropriate $C_3$ or $C_6$ lower secondary alkanol or a $C_4$ alkenol in the presence of an acid such as sulfuric acid according to the reaction:

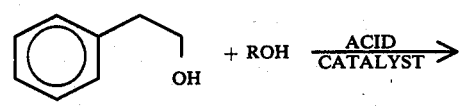

Alternatively, sodium phenethyl alcoholate may be reacted with a $C_3$ or $C_6$ secondary alkyl chloride or a $C_4$ alkenyl chloride or a sodium alkyl alcoholate or a sodium alkenyl alcoholate may be reacted with β-phenylethyl chloride or β-phenylethyl bromide by means of a "Williamson" synthesis, conventional in the organic chemistry art.

A novel aspect of our invention lies in the preparation of the isopropyl phenethylether of our invention having the structure:

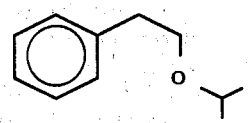

When isopropyl alcohol is reacted with phenylethyl alcohol, not all of the phenylethyl alcohol will react and thus, a mixture of phenylethyl alcohol having the structure:

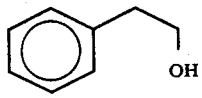

and isopropyl phenethylether having the structure:

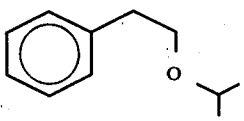

is formed.

Another aspect of our invention involves the production of the isopropyl phenethylether. In reacting the phenylethyl alcohol having the structure:

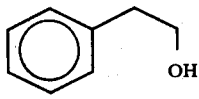

with the isopropanol in the presence of an acid catalyst, for example, sulfuric acid, a mixture of two compounds is formed: the isopropyl phenethylether and unreacted phenylethyl alcohol. It is impossible to separate this mixture whereby the isopropyl phenethylether is produced in pure form and, accordingly, we have found that the mixture of isopropyl phenethylether and phenylethyl alcohol may be easily reacted with propionic anhydride to form a mixture of isopropyl phenethylether having the structure:

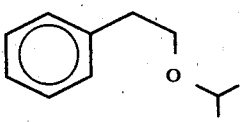

and the phenylethyl alcohol propionate having the structure:

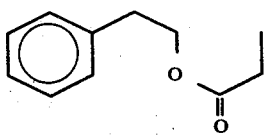

The resulting mixture of isopropyl phenethylether and phenylethyl alcohol propionate may then be easily separated by fractional separation to yield substantially pure isopropyl phenethylether in high yields. In forming the mixture of isopropyl phenethylether and phenylethyl alcohol propionate from the mixture of isopropyl phenethylether and phenylethyl alcohol with propionic anhydride, it is preferred to carry out the reaction at reflux conditions in the presence of an easily separatable solvent which is inert to the reaction mass such as toluene. The foregoing reaction sequence is illustrated as follows:

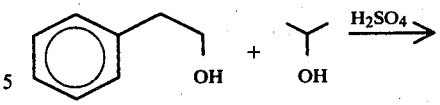

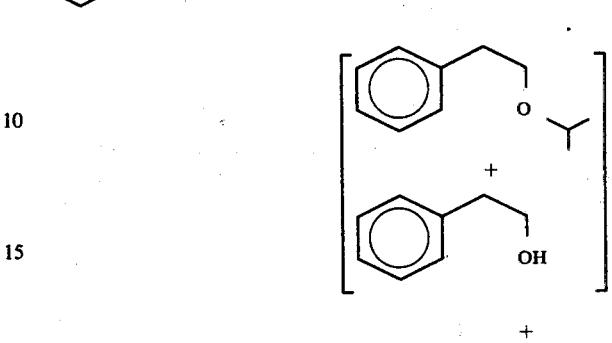

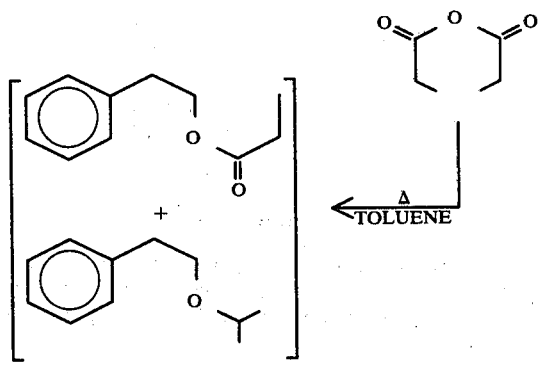

and is more specifically illustrated in Example II, infra.

Notwithstanding the pheromonal and insecticidal activity of the alkyl and/or alkenyl phenethylethers of our invention, the alkyl and/or alkenyl phenethylethers of our invention can be used to contribute long lasting green, fruity, floral, hyacinth-like, rosy, rose-hyacinth-like, galbanum-like, cassis-like and narcissus-like aromas with hyacinth/honey aromas on dry-out and with peppery and mushroomy undertones which are unexpectedly full and rich for very long periods of time, to perfumes, perfumed articles and colognes.

As olfactory agents, the alkyl and/or alkenyl phenethylethers of our invention can be formulated into or used as components of a "perfume composition" or can be used as components of a "perfumed article" or the perfume composition may be added to "perfumed articles".

The term "perfume composition" is used herein to mean a mixture of organic compounds including, for example, alcohols, aldehydes, ketones, nitriles, ethers in addition to and other than the alkyl and alkenyl phenethylethers of our invention, lactones, natural essential oils, synthetic essential oils and frequently hydrocarbons which are admixed so that the combined odors of the individual components product a pleasant or desired fragrance. Such perfume compositions usually contain (a) the main note or the "bouquet" or foundation stone of the composition; (b) modifiers which round off and accompany the main note; (c) fixatures which include odorous substances which lend a particular note to the perfume throughout all stages of evaporation, and substances which retard evaporation; and (d) top notes which are usually low-boiling, fresh-smelling materials.

In perfume compositions, the individual component will contribute its particular olfactory characteristics, but the overall effect of the perfume composition will be the sum of the effects of each of the ingredients. Thus, the alkyl and/or alkenyl phenethylethers of our invention can be used to alter the aroma characteristics of a perfume composition, for example, by highlighting or moderating the olfactory reaction contributed by another ingredient in the composition. Furthermore, the alkyl and/or alkenyl phenethylethers of our invention can be used in combination with the cyclohexyl phenethylether as claimed in earlier filed application for U.S. patent Ser. No. 192,238 filed on Sept. 30, 1980. The disclosure of said application for U.S. patent, Ser. No. 192,238 filed on Sept. 30, 1980 is hereby incorporated by reference in the instant specification. The amount of alkyl and/or alkenyl phenethylethers that may be used in conjunction with the cyclohexyl phenethylether of Ser. No. 192,238 filed on Sept. 30, 1980 may vary from about 1:99 up to about 99:1 whereby very interesting hyacinth-like, rosy, rose-hyacinth-like, galbanum-like aromas with cassis-like, narcissus-like peppery and mushroomy undertones are achieved.

The amount of alkyl and/or alkenyl phenethylether of our invention which will be effective in perfume compositions depends upon many factors, including the other ingredients, their amounts and the effects which are desired. It has been found that perfume compositions containing as little as 0.05% of the alkyl and/or alkenyl phenethylether of our invention taken alone or in combination with the cyclohexyl phenethylether, or even less can be used to impart long lasting, interesting, very strong, green, fruity, floral, hyacinth-like, rosy, rose-hyacinth-like, galbanum-like, cassis-like and narcissus aromas to soaps, liquid and solid cationic, nonionic, anionic and zwitterionic detergents, cosmetic powders, liquid and solid fabric softeners, dryer-added fabric softener articles, optical brightener compositions and other products. The amount employed can range up to 50% or more and will depend upon considerations of cost, nature of the end product and the effect desired on the finished product and particular fragrance sought.

The alkyl and/or alkenyl phenethylethers of our invention can be used alone or in a perfume composition as an olfactory component in detergents and soaps, space odorants and deodorants; perfumes; colognes, toilet waters; bath salts; hair preparations such as lacquers, brilliantines, pomades and shampoos; cosmetic preparations such as creams, deodorants, hand lotions and sun screens; powders such as talcs, dusting powders, face powder and the like. When used as an olfactory component of a perfumed article, as little as 0.01% of the alkyl and/or alkenyl phenethylether taken alone or in combination with cyclohexyl phenethylether will suffice to impart an interesting, long-lasting green, fruity, floral, hyacinth-like, rosy, rose-hyacinth-like, galbanum-like, cassis and narcissus-like aroma. Generally no more than 0.5% is required in the perfumed article.

In addition, the perfume composition can contain a vehicle or carrier for the alkyl and/or alkenyl phenethylether alone or in combination with the cyclohexyl phenethylether or in combination with still other ingredients. The vehicle can be a liquid such as an alcohol such as ethanol, a glycol such as propylene glycol or the like. The carrier can be an absorbent solid such a gum or components for encapsulating the composition such as gelatin which can be used to form a capsule wall surrounding the perfume oil by means of coacervation.

It will thus be apparent that the alkyl and/or alkenyl phenethylethers of our invention can be used to alter, modify, augment or enhance the aroma of a wide variety of consumable materials including fragrance formulations, colognes, pheromones and perfumed articles in general.

The following examples serve to illustrate our invention and this invention is to be considered restricted thereto only as indicated in the appended claims.

All parts and percentages given herein are by weight unless otherwise specified.

EXAMPLE IA

Preparation of 4-methyl-2-pentanyl Phenethylether

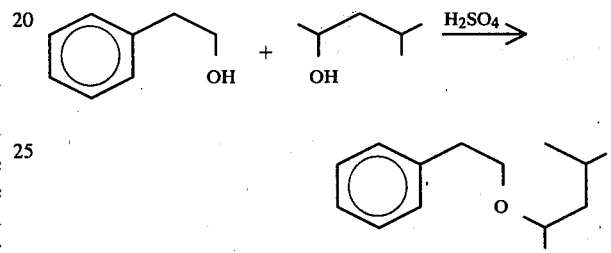

into a 3 liter reaction vessel equipped with stirrer, thermometer, reflux condenser and heating mantle is placed 732 grams of phenylethyl alcohol, 1052 grams of 4-methyl-2-pentanol and 100 grams of concentrated (93%) sulfuric acid. The reaction mass is heated to reflux and water is continuously taken off through a Bidwell trap. The reaction mass is refluxed for a period of 14 hours.

At the end of the reaction, the reaction mass is quenched with 3 liters of water, washed with aqueous sodium carbonate (saturated) and then with saturated sodium chloride (aqueous).

The reaction mass is then brushed over followed by fractional distillation to yield the following fractions:

| Fraction Number | Vapor Temp. (°C.) | Liquid Temp. (°C.) | Head Vac. mm/Hg | Reflux Ratio | Weight of Fraction |
| --- | --- | --- | --- | --- | --- |
| 1 | 40 | 80 | 4 | 9:1 | 52.7 |
| 2 | 64 | 86 | 2 | 9:1 | 48.7 |
| 3 | 68 | 90 | 2 | 9:1 | 29.1 |
| 4 | 68 | 92 | 2 | 9:1 | 27.7 |
| 5 | 68 | 93 | 2 | 9:1 | 18.7 |
| 6 | 70 | 99 | 1.8 | 9:1 | 27.4 |
| 7 | 78 | 100 | 3 | 2:1 | 27.0 |
| 8 | 80 | 105 | 2 | 2:1 | 24.8 |
| 9 | 80 | 105 | 2 | 2:1 | 27.9 |
| 10 | 80 | 105 | 2 | 2:1 | 22.4 |
| 11 | 80 | 105 | 2 | 2:1 | 28.2 |
| 12 | 80 | 105 | 2 | 2:1 | 25.5 |
| 13 | 80 | 108 | 2 | 2:1 | 27.2 |
| 14 | 87 | 114 | 2 | 2:1 | 19.5 |
| 15 | 99 | 172 | 2 | 2:1 | 26.5 |
| 16 | 93 | 220 | 3.5 | 2:1 | 14.5 |

Figure 1:
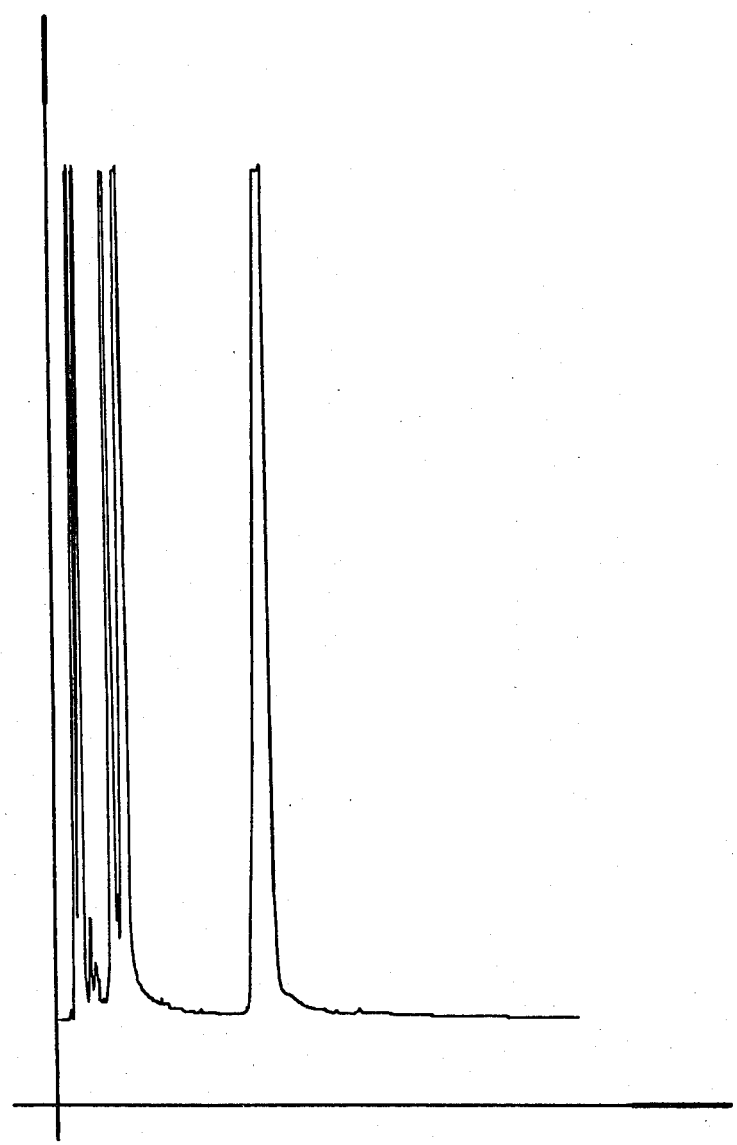
FIG. 1 is the GLC profile for the crude reaction product produced according to Example IA containing the compound having the structure.

FIG. 1 is the GLC profile for the crude reaction product produced according to Example IA containing the compound having the structure:

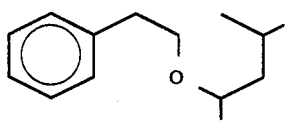

FIG. 2 is the NMR spectrum for the reaction product of Example IA containing the compound having the structure:

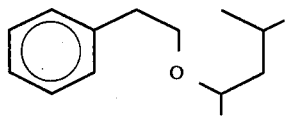

FIG. 3 is the infra-red spectrum for the reaction product of Example IA containing the compound having the structure:

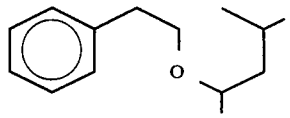

EXAMPLE IB

Preparation of 4-methyl-2-pentanyl Phenethylether

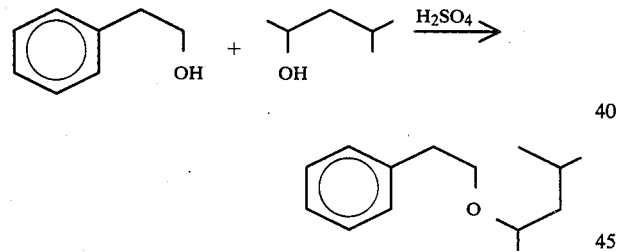

Into a 10 liter reaction vessel equipped with stirrer, thermometer, reflux condenser and heating mantle is placed 1428 grams of 4-methyl-2-pentanol; 915 grams of phenylethyl alcohol and 500 grams of sulfuric acid. The reaction mass is heated to reflux (105° C.) and refluxed for a period of 2 hours.

FIG. 4 is the GLC profile for the crude reaction mass.

EXAMPLE II

Preparation of Isopropyl Phenethylether

Reaction:

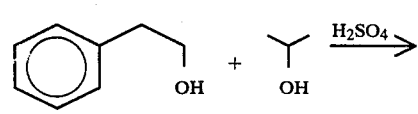

Into a 10 liter reaction flask is placed 1440 grams of isopropyl alcohol and 732 grams of phenylethyl alcohol. Over a period of 1 hour, a solution of 270 grams of sulfuric acid and 30 ml water is added slowly. At the end of the addition of the sulfuric acid solution, the reaction mass is heated to reflux and the reaction mass is refluxed for a period of 4 hours. At the end of the 4 hour period, three liters of water is added to the reaction mass and the reaction mass is neutralized with 50% sodium hydroxide. One liter of toluene is added and the toluene layer is separated from the aqueous layer.

To the toluene mixture is added 260 grams of propionic anhydride and the propionic anhydride/toluene/phenylethyl alcohol/isopropyl phenethylether mixture is then refluxed for a period of 30 minutes. The reaction mass is then cooled down and one liter of water is added thereto. The reaction mass is then washed with 50% caustic followed by saturated sodium chloride and then neutralized with saturated sodium bicarbonate.

The reaction mass is then distilled yielding the following fractions:

| Fraction Number | Vapor Temp. (°C.) | Liquid Temp. (°C.) | Head Vac. mm/Hg. | Weight of Fraction |
|---|---|---|---|---|
| 1 | 24/70 | 24/101 | 1.8/1.8 | 4.2 |
| 2 | 70 | 101 | 1.4 | 12.4 |
| 3 | 60 | 101 | 1.1 | 14.5 |
| 4 | 65 | 102 | 1.1 | 21.0 |
| 5 | 65 | 104 | 1.0 | 27.8 |
| 6 | 60 | 86 | 1.0 | 22.3 |
| 7 | 58 | 110 | 1.3 | 26.3 |
| 8 | 59 | 112 | 1.3 | 26.8 |
| 9 | 64 | 113 | 1.3 | 23.9 |
| 10 | 65 | 113 | 1.4 | 25.8 |
| 11 | 70 | 115 | 1.3 | 28.2 |
| 12 | 72 | 115 | 1.3 | 29.2 |
| 13 | 74 | 115 | 1.3 | 29.6 |
| 14 | 76 | 116 | 1.3 | 30.0 |
| 15 | 77 | 116 | 1.3 | 29.3 |
| 16 | 76 | 115 | 1.2 | 29.1 |

-continued

| Fraction Number | Vapor Temp. (°C.) | Liquid Temp. (°C.) | Head Vac. mm/Hg. | Weight of Fraction |
|---|---|---|---|---|
| 17 | 76 | 115 | 1.2 | 27.7 |
| 18 | 76 | 115 | 1.2 | 28.9 |
| 19 | 77 | 116 | 1.2 | 28.9 |
| 20 | 77 | 116 | 1.2 | 29.5 |
| 21 | 78 | 117 | 1.2 | 27.8 |
| 22 | 79 | 117 | 1.2 | 29.6 |
| 23 | 79 | 117 | 1.2 | 25.0 |
| 24 | 82 | 126 | 1.2 | 25.0 |
| 25 | 83 | 128 | 1.2 | 27.1 |
| 26 | 85 | 156 | 1.2 | 29.2 |
| 27 | 106 | 250 | 1.2 | 18.9 |

FIG. 5 is the GLC profile for the crude reaction product of Example II prior to propionic anhydride reaction containing the compounds having the structures:

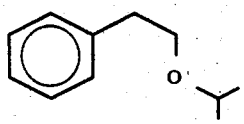 and 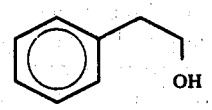

FIG. 6 is the GLC profile for fraction 4 of the distillation product of the reaction product of Example II after reaction with propionic anhydride, containing the compound having the structure:

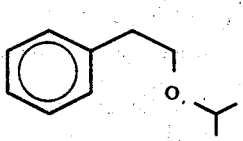

FIG. 7 is the NMR spectrum for the reaction product of Example II after distillation containing the compound having the structure:

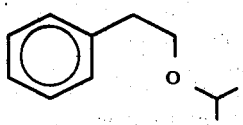

FIG. 8 is the infra-red spectrum for the reaction product of Example II after distillation after reaction with propionic anhydride containing the compound having the structure:

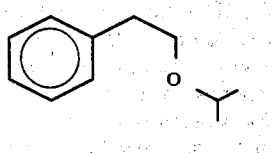

EXAMPLE III

Prearation of 2-butenyl Phenethylether and 1-methallyl Phenethylether

Reaction:

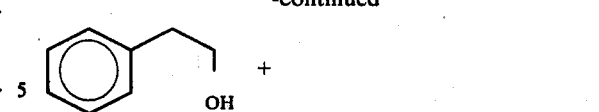

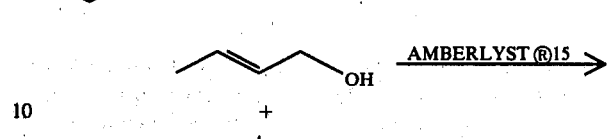

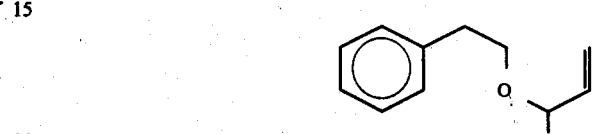

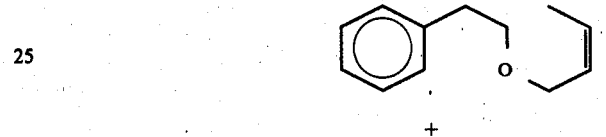

Crotyl alcohol (216 grams) is slowly added to a stirred slurry of phenylethyl alcohol (366 grams) and Amberlyst ® 15 (cation exchange resin manufactured by the Rohm & Haas Company, Philadelphia, Pa.; an acid cation exchange resin which is sulfonated polystyrene) at 100° C. The reaction mass is aged at 100° C. for a period of 5 hours whereupon the solution is cooled and filtered. The organic solution is washed with 25% aqueous sodium hydroxide. The GLC profile of the crude reaction product is set forth in FIG. 9 (conditions: 10% SE-30 packed column programmed at 120°-220° C. at 8° C. per minute). Peak 3 is the peak for phenylethyl alcohol; peak 4 is the peak for the 1-methallyl phenethylether; peak 5 is the peak for 2-butenyl phenethylether (cis and trans isomers).

A portion of the product is isolated by GLC preparative chromatography.

FIG. 10A represents the NMR spectrum for peak 4 of the GLC profile of FIG. 9 containing the compound having the structure:

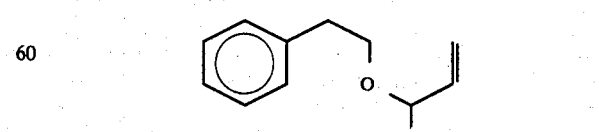

FIG. 10B is the infra-red spectrum for peak 4 of FIG. 9 which is the GLC profile for the reaction product of Example III, containing the compound having the structure:

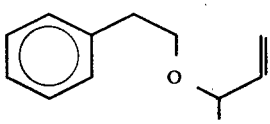

FIG. 11A is the NMR spectrum for peak 5 of FIG. 9 which is the GLC profile for the reaction product of Example III, containing the compounds having the structures:

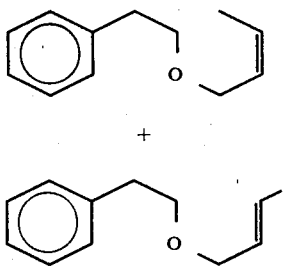

FIG. 11B is the infra-red spectrum for peak 5 of FIG. 9 which is the GLC profile of Example III, containing the compounds having the structures:

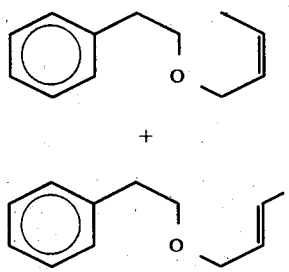

EXAMPLE IV

Field tests are made each time using 100 male and 100 female *Lasioderma serricorne* (F.) cigarette beetles. The beetles were released at a certain distance from the source of attraction which was treated with either of 1,3-dimethyl butyl phenethylether prepared according to Example IA, isopropyl phenethylether prepared according to Example II or the mixture of 2-butenyl phenethylether and 1-methallyl phenethylether prepared according to Example III. Further, felled trees having already been contaminated with the respective beetles are positioned at both sides of the starting point. After a certain period of time the amount of insects gathered at the source of attraction was determined thus indicating the effectiveness of the pheromonal mixtures according to the invention.

Field tests with *Lasioderma serricorne* (F.) are made whereby the distance between the starting point and the source of attraction is 50 meters. Four independent field tests were made whereby 42% of the male beetles and 46% of the female beetles gathered at each catch tree. The concentration of insects at the catch tree was 58% of the male insects and 59% of the female insects. In all these tests the catch tree was impregnated with 0.7% ethanolic solutions of one of the following materials:

(a) 1,3-dimethyl butyl phenethylether prepared according to Example IA (b) isopropyl phenethylether prepared according to Example II (c) a mixture of 2-butenyl phenethylether and 1-methallyl phenethylether prepared according to Example III (7 grams of phenethylether derivative per 92 grams of 95% aqueous ethanol).

EXAMPLE V

During two consecutive days several felled oak trees surrounding a field of tobacco plants were treated with 250 mg of:

(a) 1,3-dimethyl butyl phenethylether prepared according to Example IA (b) isopropyl phenethylether prepared according to Example II (c) a mixture of 2-butenyl phenethylether and 1-methallyl phenethylether prepared according to Example III in 1.0% ethanolic solution. These trees were exposed in an area which were contaminated with *Lasioderma serricorne* (F.). After 3 to 4 days, 115 beetles per square meter were observed on the logs. Other untreated logs or trees in the direct neighborhood of the treated logs or trees showed very few (about 12) insects per square meter on the average while other trees at a distance of 10 to 20 meters showed no contamination.

EXAMPLE VI

In a large test field, mixtures of either:

(a) 1,3-dimethyl butyl phenethylether prepared according to Example IA (b) isopropyl phenethylether prepared according to Example II (c) a mixture of 2-butenyl phenethylether and 1-methallyl phenethylether prepared according to Example III in admixture with different DDT preparations, fluorine-containing mixtures and arsen-containing mixtures as well as hexachloro-cyclohexane were used. These mixtures contained also small amounts of surface-active agents and carriers. The mixtures were applied to catch trees namely logs of oak trees in an area of tobacco plants contaminated with *Lasioderma serricorne* (F.). The distance between the catch trees was always 200 meters. After 8 days there was no contamination either in the tobacco fields or around the oak trees. About 93% of the *Lasioderma serricorne* (F.) insects were destroyed. Surprisingly, it was found that after the fourth day the attracting effect was not diminished in spite of the dead insects being present. Furthermore, in those areas where the phenethylether derivatives of either Examples IA, II or III was used alone, the average number of insects destroyed was about 78% which in itself is surprising. Thus, the phenethylether derivatives of either Examples IA, II or III not only act as pheromones but also as insecticides. Furthermore, the entire area wherein the phenethylether derivatives of either Example IA, II or III were used had faint, pleasant, floral aromas covering any adverse and esthetically displeasing aromas of any other insecticides that were used.

EXAMPLE VII

The following mixture is prepared:

| Ingredients | Parts by Weight |
| --- | --- |
| Phenylacetic acid | 70.0 |
| Coumarin | 20.0 |
| Phenylethylphenyl acetate | 100.0 |
| Phenylethyl alcohol | 5.0 |
| Benzyl benzoate | 100.0 |
| Dimethylphenylethyl carbinol | 10.0 |
| Methyl anthranilate | 5.0 |
| Beta ionone | 10.0 |
| either: | |
| (a) 1,3-dimethyl butyl phenethylether prepared according to Example IA; or | |
| (b) isopropyl phenethylether prepared according to Example II; or | |
| (c) the mixture of 2-butenyl phenethylether and 1-methallyl phenethylether prepared according to Example III | 30.0 |

The 1,3-dimethyl butyl phenethylether prepared according to Example IA imparts the fruity, floral, hyacinth, rose aroma to this honey fragrance while giving it a very warm undertone in imparting a very long-lasting rose topnote to this fragrance.

The isopropyl phenethylether prepared according to Example II imparts the strong green, floral, fruity, hyacinth aroma with a slight peppery, mushroom undertone to this honey fragrance.

The mixture of 2-butenyl phenethylether and 1-methallyl phenethylether produced according to Example III imparts the green, floral aroma to this honey fragrance.

EXAMPLE VIII

Preparation of a Cosmetic Powder Composition

A cosmetic powder is prepared by mixing in a ball mill 100 grams of talcum powder with 0.25 grams of one of the perfume compositions prepared according to Example VII. Each of the perfume compositions has an excellent floral aroma.

EXAMPLE IX

Perfumed Liquid Detergent

Concentrated liquid detergents (lysine salt of n-dodecylbenzene sulfonic acid as more specifically described in U.S. Pat. No. 3,948,818 issued on Apr. 6, 1976) with floral aroma nuances are prepared containing 0.10%, 0.15%, and 0.20% of each of the fragrances prepared according to Example VII. They are prepared by adding and homogeneously admixing the appropriate quantity of one of the three fragrance formulations prepared according to Example VII in the liquid detergents. The detergents all possess excellent floral aromas, the intensity increasing with greater concentrations of perfume composition prepared according to Example VII.

EXAMPLE X

Preparation of a Cologne and Handkerchief Perfume

The compositions prepared according to Example VII are incorporated into colognes at concentrations of 2.0%, 2.5%, 3.0%, 4.0%, 4.5% and 5.0% in 80%, 85%, 90% and 95% aqueous food grade ethanol; and into handkerchief perfumes at concentrations of 15%, 20% and 30% (in 80%, 85% and 95% aqueous food grade ethanol). Distinctive and definitive strong, floral aromas are imparted to the colognes and to the handkerchief perfumes at all levels indicated.

EXAMPLE XI

Preparation of Soap Composition 100 grams of soap chips are mixed with 1 gram of each of the formulations of Example VII until homogeneous compositions are obtained. The homogeneous compositions are each heated under three atmospheres pressure at 180° C. for periods of 3 hours and the resulting liquids are placed into soap molds. The resulting soap cakes, on cooling, manifest excellent floral aromas that are very long lasting.

EXAMPLE XII

Preparation of a Solid Detergent Composition

A detergent is prepared from the following ingredients according to Example I of Canadian Pat. No. 1,007,948:

| | Percent by Weight |
| --- | --- |
| "Neodol 45-11" (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed with 0.15 gram samples of each of the three honey based perfumes of Example VII. Each of the detergent samples have excellent floral, honey-like aromas.

EXAMPLE XIII

Dryer-Added Fabric Softener Article

Utilizing the procedure of Example I at column 15 of U.S. Pat. No. 3,632,396, a nonwoven cloth substrate useful as a dryer-added fabric softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):

57% $C_{20-22}$ HAPS
22% isopropyl alcohol
20% antistatic agent
1% of the phenethylether substances as set forth in Table I below Fabric softening compositions prepared as set forth above having aroma profiles as set forth in Table I below each consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1. Aromas are imparted in a pleasant manner to the head space in the dryer on operation thereof using said dryer-added fabric softening nonwoven fabric.

TABLE I

| Phenethylether Derivative | Organoleptic Properties in Head Space above Dryer and of Dryer-Added Fabric Softener Article per se |
|---|---|
| 1,3-dimethyl butyl phenethylether produced according to Example I. | A galbanum, cassis-like, rosy, hyacinth and narcissus aroma. |
| Isopropyl phenethylether prepared according to Example II. | A strong, green, floral, fruity, hyacinth aroma with a slight peppery and mushroomy undertone with honey/hyacinth topnotes. |
| Mixture of 2-butenyl phenethylether and 1-methallyl phenethylether produced according to Example III. | A green, floral aroma. |

EXAMPLE XIV

A liquid detergent composition prepared according to Example IV of United Kingdom Pat. No. 1,498,520 whereby the following ingredients are admixed:

| Ingredient | Weight % |
|---|---|
| Coconut alcohol ethoxylate | 30 |
| Linear alkyl benzene sulfonate, triethanolamine salt (alkyl = $C_{11.8}$ avg.) | 10 |
| Potassium chloride | 3 |
| Triethanolamine | 3 |
| Triethanolammonium citrate | 2 |
| Ethyl alcohol | 5 |
| Soil release ether "D" | 1.0% |
| Phenethylether derivative as set forth in Table II below | 3.0 |
| Water | Balance |

The soil release ether "D" is defined according to Table II on page 15 of United Kingdom Pat. No. 1,498,520.

This composition is prepared by admixing all of the ingredients exclusive of soil release ether "D" and agitating the mixture until all electrolytes are dissolved. Soil release ether "D" is then admixed with the solution in the form of a dry powder which passes through a 150 mesh standard sieve. The resulting composition is in the liquid state and is easily pourable. The composition is found not to redden on contact with plastic bottles, does not gel with water and has an aroma as set forth in Table II below which lasts for several weeks when exposed to the atmosphere.

TABLE II

| Phenethylether Derivative | Organoleptic Properties of Detergent Composition |
|---|---|
| 1,3-dimethyl butyl phenethylether produced according to Example I. | A galbanum, cassis-like, rosy, hyacinth and narcissus aroma. |
| Isopropyl phenethylether prepared according to Example II. | A strong, green, floral, fruity, hyacinth aroma with a slight peppery and mushroomy undertone with honey/hyacinth topnotes. |
| Mixture of 2-butenyl phenethylether and 1-methallyl phenethylether produced according to Example III. | A green, floral aroma. |

The foregoing compositions are added to an aqueous laundrying bath at concentrations of 0.20% (weight) each at a temperature of 55° C., water hardness 7 grains per gallon and a pH of 10.0. Polyester and mixed polyester/cotton fabrics are laundered in the bath for a period of 10 minutes after which the fabrics are thoroughly rinsed with fresh water and dried at ambient temperatures. The fabrics are provided with a soil release finish. The head space above the fabrics have pleasant aromas as described in Table II above and are also rather long-lasting (about 3 days).

EXAMPLE XV

Preparation of Cosmetic Powder Compositions

Cosmetic powders are prepared by admixing in a ball mill, 100 grams of talcum powder with 0.25 grams of the phenethylether derivative as set forth in Table III below. The resulting cosmetic powders have aromas as set forth in Table III below which are very long-lasting.

TABLE III

| Phenethylether Derivative | Organoleptic Properties of Cosmetic Powder |
|---|---|
| 1,3-dimethyl butyl phenethylether produced according to Example I. | A galbanum, cassis-like, rosy, hyacinth and narcissus aroma. |
| Isopropyl phenethylether prepared according to Example II. | A strong, green, floral, fruity, hyacinth aroma with a slight peppery and mushroomy undertone with honey/hyacinth topnotes. |
| Mixture of 2-butenyl phenethylether and 1-methallyl phenethylether produced according to Example III. | A green, floral aroma. |

EXAMPLE XVI

Perfumed Liquid Detergent

Concentrated liquid detergents (lysine salt of n-dodecylbenzene sulfonic acid as more specifically described in U.S. Pat. No. 3,948,818 issued on Apr. 6, 1976) with aromas as set forth in Table IV below are prepared containing 0.10%, 0.15%, 0.20% and 0.25% of the phenethylether derivatives as set forth in Table IV below. They are prepared by adding and homogeneously admixing the appropriate quantities of phenethylether derivatives in the liquid detergent. The detergents all possess intense and long-lasting aromas as set forth in Table IV below.

TABLE IV

| Phenethylether Derivative | Detergent Aroma Profile |
|---|---|
| 1,3-dimethyl butyl phenethylether produced according to Example I. | A galbanum, cassis-like, rosy, hyacinth and narcissus aroma. |
| Isopropyl phenethylether prepared according to Example II. | A strong, green, floral, fruity, hyacinth aroma with a slight peppery and mushroomy undertone with honey/hyacinth topnotes. |
| Mixture of 2-butenyl phenethylether and 1-methallyl phenethylether produced according to Example III. | A green, floral aroma. |

EXAMPLE XVII

Preparation of Colognes and Handkerchief Perfumes

Phenethylether derivatives as set forth in Table V below are incorporated into colognes at concentrations of 2.0%, 2.5%, 3.0%, 3.5%, 4.0% and 4.5% in 80%, 85%, 90% and 95% aqueous food grade ethanol; and into handkerchief perfumes at concentrations of 15%, 20%, 25% and 30% (in 80%, 90% and 95% aqueous ethanol solutions). Distinctive aromas as set forth in Table V below which are very long-lasting on dry-out (44 hours) are imparted to the colognes and to the handkerchief perfumes at the various above levels indicated.

TABLE V

| Phenethylether Derivative | Organoleptic Properties of Colognes and Handkerchief Perfumes |
|---|---|
| 1,3-dimethyl butyl phenethylether produced according to Example I. | A galbanum, cassis-like, rosy, hyacinth and narcissus aroma. |
| Isopropyl phenethylether prepared according to Example II. | A strong, green, floral, fruity, hyacinth aroma with a slight peppery and mushroomy undertone with honey/hyacinth topnotes. |
| Mixture of 2-butenyl phenethylether and 1-methallyl phenethylether produced according to Example III. | A green, floral aroma. |

What is claimed is:

1. A method of attracting and destroying *Lasioderma serricorne* (F.) comprising applying to an area contaminated with said *Lasioderma serricorne* (F.) at least one phenethylether defined according to the structure:

wherein R is $C_4$ alkenyl, said attractant being applied to said area in an amount sufficient to attract said *Lasioderma serricorne* (F.).

2. The method of claim 1 wherein the amount of said attractant applied to said area is in an amount (a) sufficient to attract said *Lasioderma serricorne* (F.) and (b) sufficient to substantially destroy said *Lasioderma serricorne* (F.) thus attracted.

3. The method of claim 1 wherein the attractant applied to the area is in an amount (a) sufficient to attract said *Lasioderma serricorne* (F.), (b) sufficient to destroy said *Lasioderma serricorne* (F.) substantially, and (c) sufficient to negate any adverse aromas of any other materials in said area and augment or enhance or impart a floral aroma to said area.

* * * * *